United States Patent [19]

Yoon

[11] Patent Number: 4,655,208
[45] Date of Patent: Apr. 7, 1987

[54] FAST-SETTING CASTING TAPE

[75] Inventor: Hee K. Yoon, North Brunswick, N.J.

[73] Assignee: Johnson & Johnson Products Inc., New Brunswick, N.J.

[21] Appl. No.: 838,980

[22] Filed: Mar. 12, 1986

[51] Int. Cl.$^4$ .............................................. A61L 15/00
[52] U.S. Cl. .................................................... 128/156
[58] Field of Search ...................... 128/156, 89, 91, 90; 428/260, 266; 523/111; 427/2

[56] References Cited

U.S. PATENT DOCUMENTS

| 4,309,990 | 1/1982 | Brooks ................................ 128/90 |
| 4,427,003 | 1/1984 | Fennimore ........................... 128/90 |
| 4,433,680 | 2/1984 | Yoon .................................... 128/90 |

Primary Examiner—Gregory E. McNeill
Attorney, Agent, or Firm—Michael Q. Tatlow

[57] ABSTRACT

A fast setting casting tape made with a polyurethane prepolymer prepared with a hydrophilic polyol and an isocyanate. The casting tape has faster setting times than casting tapes made with hydropholic polyols.

10 Claims, No Drawings

FAST-SETTING CASTING TAPE

FIELD OF THE INVENTION

The present invention relates to an improved polyurethane orthopedic casting tape used to form orthopedic bandages and which will set in a relatively short period of time.

BACKGROUND OF THE INVENTION

Plaster of Paris casts have been used to immobilize body members for some time. These bandages are made by depositing plaster of Paris on a reinforcing scrim material such as gauze. When the plaster of Paris is dipped in water, the alphahemihydrate of calcium sulfate is converted to calcium sulfate dihydrate, which results in the hardening of the cast. Plaster of Paris casts, however, suffer from a number of disadvantages. X-ray transmission through the cast to determine whether a fracture has been properly set is extremely difficult. In addition, the cast is quite heavy and restricts the mobility of the patient wearing the cast. The casts are also very sensitive to water and may seriously lose their load-bearing capability if they become wet. In addition, the air permeability of the plaster of Paris cast is very limited, and, as a result, they do not allow evaporation of moisture from the skin beneath the cast, which may result in skin irritation beneath the cast.

In order to overcome the disadvantages of plaster of Paris casts, numerous attempts have been made to develop plastic or plastic-reinforced materials as a replacement for plaster of Paris.

U.S. Pat. Nos. 3,241,501 and 3,881,473 disclose casts which are made with a flexible fabric impregnated with a polymer which is capable of being cured by ultaviolet light. Although this casting material overcomes some of the disadvantages of plaster of Paris cast material, it requires a different technique in its application and also requires the use of an ultraviolet light source in order to cure the cast. These casts also require significantly longer times for the cast to set before they will be load bearing.

More recent attempts to produce substitutes for plaster of Paris include the casting tapes made with polyurethane prepolymers which are disclosed in U.S. Pat. Nos. 4,376,438; 4,427,001; and 4,411,262. These casting tapes are made from relatively open weave fabrics coated with polyurethane prepolymers, that is, reaction products of isocyanates and polyols. The bandages are dipped into water in the same manner as the plaster of Paris bandages and then applied to the limb of a patient. The water causes the prepolymer to polymerize and form a rigid polymer structure which will support the broken limb. In order to obtain the desired rapid hardening or setting of the bandage, there are usually catalyst systems employed in the prepolymer formulation. The above-mentioned U.S. Pat. No. 4,376,438 employs an amino polyol which in effect is a catalyst built into the polyol portion of the polyurethane. The above-mentioned U.S. Pat. Nos. 4,411,262 and 4,427,002 employ added catalysts such as amines to catalyze the hardening of the polyurethane prepolymer. U.S. Pat. Nos. 4,433,680 discloses a similar diisocyanate polyol composition which employs a dimorpholinediethylether as the catalyst.

The polyurethane prepolymer casting tapes described above have met with considerable acceptance as a replacement for plaster of Paris. The general properties of the casting tapes and the finished casts have been found to be acceptable to both physicians and patients and offer advantages over plaster of Paris cast bandages.

One of the problems connected with the manufacture of such polyurethane casting tapes is the balance between the gel time of the casting tapes on storage and the set time of the casting tapes after they are activated with water and applied to the patient. If the catalyst concentrations are excessive or if certain types of catalysts are used to cause the casting tape to set quickly, there is a danger that the polyurethane will gel or precure while it is still in the package which results in an unacceptable shelf life for the product. The mere reduction of the catalyst levels of certain types of catalysts will overcome this problem, but may result in very long set times for the finished cast on the patient. The set time is generally the time which it takes for the cast to harden and it must be relatively hard before any weight can be put on the cast by the patient. p Another problem with such casting tapes is that the set times are generally too long to be employed in certain situations. With the casting of the broken limbs on infants the set time must be quite short in order to ensure that the casting tape will harden before the limb of the patient is moved.

SUMMARY OF THE INVENTION

The present invention relates to a polyurethane casting tape which comprises the usual fibrous substrate coated with a polyurethane prepolymer and which will set in less time than the previously available polyurethane casting tapes. The cast material is also very stable on storage. The prepolymer formulation may contain any of the catalyst systems previously employed in casting tapes without adversely affecting the storage properties or the set times of the casting tape.

DETAILED DESCRIPTION OF THE INVENTION

Isocyanates

The aromatic isocyantes useful in the prepolymer system of the present invention may be any of the aromatic polyisocyanates known in polyurethane chemistry which are described, for example, in "Polyurethanes, Chemistry and Technology," Part I, Interscience Publishers (1962).

The aromatic polyisocyanates preferred include toluene diisocyanate (TDI), such as the 80/20 or the 65/35 isomer mixture of the 2,4 and 2,6 isomeric forms; diphenylmethane diisocyante (MDI), such as the 4,4', and 2,4' and the 2,2' isomeric forms or isomeric mixtures thereof; modified MDI containing additional functional groups such as carbodiimide groups, urethane groups and allophanate groups and polymethylene polyphenylisocyanates (Polymeric MDI) which are derived from phosgenation of the condensation products of aniline and formaldehyde. Most preferred polyisocyanate is the carbodiimide containing MDI which is readily available commercially, e.g., Isonate 143L and Rubinate XI-168.

Polyols

The polyols useful in the prepolymer system of the present invention differ somewhat from the polyols used in the prior art casting tapes. The polyols used in the present casting tapes are characterized herein as hydrophilic polyols. The use of these hydrophilic polyols results in increased hydrophilicity of the prepolymer formulation. The increased hydrophilicity of the prepolymer formulation causes the water into which the casting tape is dipped to rapidly migrate or diffuse into the prepolymer. The more rapid diffusion of the water causes the casting tape to harden in a shorter period of time then has heretofore been obtained. Generally, the polyols which have previously been used have been hydrophobic polyols which resist the rapid takeup of the prepolymer of water used to activate the curing of the prepolymer in the casting tape. These previously employed polyols have generally been polyether polyols which are made by the polymerization of propylene oxide or combinations of ethylene oxide and propylene oxide in which the propylene oxide is present in a high enough quantity to result in a hydrophobic polyol.

The preferred hydrophilic polyols employed in the present invention are poly(oxyalkyl) alcohols of the formula:

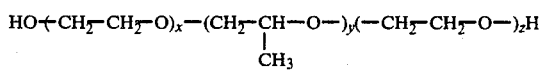

in which x is at least 1 and y is between 3 and 42, and z may be 0 and x+z are between 1 and 13.

The hydrophilic polyols are generally homopolymers of ethylene oxide or random or block copolymers of ethylene oxide with propylene oxide in which the propylene oxide is present in an amount no more that 80% by weight and preferably no more than 65% by weight thereby resulting in a polyol which has hydrophilic characteristics and referred herein as a hydrophilic polyol. The polyol of the present invention may also be a copolymer of ethylene oxide with tetramethylene oxide in which the tetramethylene oxide is present in no more than 70% by weight in the copolymer and which results in a polyol which is hydrophilic. Other hydrophilic polyols that may be used are polyester polyols which have been capped with ethylene oxide and ethylene oxide adducts of castor oil, glycerol and 1,1,1-trimethylol propanol. Generally, the molecular weight range of the polyols useful in the present invention are between 200 and 6,000 and preferably between 600 and 2,000. The polyols have a functionality, i.e., OH group of at least 2 and preferably 2 or 3. The polyol may also be a mixture of a hydrophobic homopolymer, e.g., propylene oxide, and a hydrophilic homopolymer, e.g., ethylene oxide. In the use of the mixtures, the hydrophobic polyol should be no more than 80% and preferably no more than 60% of the total weight of the polyols.

The preferred polyurethane prepolymer used in the present invention is made from diphenylmethanediisocyanate containing carbodiimide groups. These diisocyanates are reacted with the hydrophilic polyol containing two or three functional groups. The preferred polyols are homopolymers of ethylene oxide having a molecular weight of 1,000.

The ratio of the polyisocyanate to the polyol in the prepolymer is best expressed by the equivalent ratio. Equivalent weight is determined by dividing the molecular weight of each particular component by its functionality or number of functional groups in the compound. The equivalency ratio is the ratio of the equivalence of the isocyanate to the polyol in the composition. The equivalent ratio in the present system should be between 2:1 to approximately 15:1 equivalents of the polyisocyanate to the polyol and preferably from 2:1 to 10:1. These components are combined so that there is an excess of from 5% to 30% NCO groups in the prepolymer.

The prepolymer formulation of the present invention will also contain from 0.1% to about 10% by weight based on the total weight of the mixture of a catalyst. The catalyst may be an amine such as dimethylethanolamine (DMEA) or a mixture of DMEA and bis(2-dimethylaminoethyl)ether or a dimorpholinodialkylether. The preferred catalyst is the dimorpholinodiethylether catalyst disclosed in U.S. Pat. No. 4,433,680.

In addition to the polyisocyanate, the polyol and the catalyst, the prepolymer reactants may also include a small amount i.e., 0.01% to 1% by weight of a stabilizer such as benzoyl chloride and a small amount of a surfactant agent such as a silicone liquid which is used as an antifoam agent to prevent the foaming of the prepolymer composition. The antifoam agent is generally present in an amount of from 0.01% to 1% by weight.

The set times of casting tapes of the present invention are generally at least one minute to one and one-half minutes less than the set times of prior art casting tapes. The set times of the present tapes are between 2.5 to 3.5 minutes and the set times of the prior art tapes are between 4 and 6 minutes but may be more than 6 minutes.

The prepolymer of the present invention is formed in the same manner as prepolymers of other casting tapes. Typical conditions for the formation of the prepolymer is as follows:

A reaction vessel is placed under a vacuum and the isocyanate component is added to the vessel. The vacuum is released and nitrogen is added to the vessel and the antifoam agent is added to the isocyanate component. The stabilizer, benzoyl chloride is added to the vessel and mixed thoroughly with the reactants in the vessel. Vacuum dried hydrophilic polyols containing the catalyst are then added to the reaction vessel over a period of from 20 to 25 minutes. The reaction temperature is maintained between 50° C. and 60° C. for approximately one hour. The completion of the reaction can be determined by obtaining a sample of the reaction product and testing for the desired level of NCO in the prepolymer.

The prepolymer is then applied in a dry atmosphere i.e., in the absence of atmospheric moisture, to a substrate by reverse roll coating or other coating techniques to form the casting tape. The fibers in the fabric may be synthetic fibers such as a polyester, or natural fibers such as cotton or mixtures thereof. The preferred fiber in the substrate is fiberglass. The substrate may be a knitted or woven fabric having the weight of between approximately 150 to 450 grams per square meter and preferably between 260 and 360 grams per square meter. Suitable fabrics for the substrate include those disclosed in U.S. Pat. Nos. 3,882,857; 3,787,272 and 4,134,397. The weight of the prepolymer on a fiberglass fabric is generally between 60 to 450 grams per square meter, preferably between 150 to 250 grams per square meter. Because of the reactivity of the prepolymer composition with atmospheric moisture, immediately after the prepolymer is applied to the fabric, the coated fabric is packaged in an inert atmosphere in a moisture impervious package to prevent contact with atmospheric moisture.

When the casting tape is to be used, it is removed from the package and placed in water from 3 to 30 seconds, preferably between 5 and 10 seconds. It is removed from the water and applied to the patient, usually over a tubular, knitted fabric and a cast padding. The casting tape of the present invention will set in approximately 3 minutes or less.

The set time or setting time of the casting tape in the laboratory can be determined by dipping the casting tape in water at 75° F. and squeezing the bandage 4 or 5 times under the surface of the water. A test cylinder is then formed by wrapping successive layers of the tape around a 2¾ inch wooden or metal dowel. The set time is determined by attempting to indent the test cylinder by fingernail pressure. At the time when the test cylinder cannot be indented, the set time is recorded.

In the following examples, the crush strength of the casting tapes was determined by the formation of test cylinders set forth above. The samples are removed from the dowel and compressed a distance of one centimeter and the load necessary to deflect the test cylinder is determined. The test cylinders for fiberglass casting tapes are made by wrapping five layers of a 4-inch casting tape around a 2¾ inch metal or wooden dowel. For nonfiberglass casting tapes, 15 layers of casting tape are wrapped around a 2¾ inch dowel. The cylinders are aged and the crush strength is determined at different time points.

EXAMPLE I

A series of prepolymers were prepared with a carbodiimide containing MDI commercially available as Isonate ™ 143L. The polyol employed was a hydrophilic polyol sold by Olin Chemical Corp. under the designation Poly G 76-120 and is a copolymer made from 33% by weight ethylene oxide and 67% by weight propylene oxide. The catalyst employed was dimorpholinodiethylether. The prepolymer was coated on a knitted polyester substrate and test cylinders were prepared. The set times for the prepolymer and crush strength of the cylinders were determined. The weights of the cylinders were 49±2 grams. The formulations and the results of the tests are shown in Table I. The ingredients are listed in grams unless otherwise noted.

TABLE I

| Formulation | a | b | c |
|---|---|---|---|
| Isonate 143L | 547 | 608 | 547 |
| Poly G 76-120 | 409 | 409 | 409 |
| Catalyst | 19 cc | 20.3 cc | 24 cc |
| Benzoyl Chloride | 0.4 cc | 0.42 cc | 0.4 cc |
| Silicone oil (DC-200) | 0.7 | 0.75 | 0.7 |
| Set time (minutes) | 2.8 | 2.6 | 2.5 |
| Crush Strength-lbs. | | | |
| 15 minutes | 59 | 76 | 49 |
| 1 hour | 76 | 89 | 55 |
| 24 hours | 94 | 102 | 71 |

EXAMPLE II

A series of prepolymers were prepared with a carbodiimide containing MDI, commercially available as Isonate 143L. The polyol employed was a mixture of diol, Poly G 55-173 and the triol Poly G 76-120. Poly G 55-173 is a diol containing 45% ethylene oxide and 55% propylene oxide. The catalyst was dimorpholinodiethylether. The prepolymer was coated on a fiberglass substrate at a coating weight of 200 grams per square meter and test cylinders were prepared. The weights of the test cylinders were 59±2 grams. The set time and the crush strength were determined. The formulations and the results of the tests are shown in Table II. The ingredients are listed in grams unless otherwise noted.

TABLE II

| Formulation | a | b | c | d |
|---|---|---|---|---|
| Isonate 143L | 644 | 572 | 572 | 624 |
| Poly G 55-173 | 194 | 194 | 233 | 268 |
| Poly G 76-120 | 187 | 187 | 152 | 175 |
| Benzoyl Chloride | 0.43 cc | 0.4 cc | 0.4 cc | 0.44 cc |
| Silicone Oil (DC-200) | 0.77 | 0.71 | 0.72 | 0.8 |
| Catalyst | 17.9 | 16.7 | 16.7 | 18.7 |
| Set Time (Minutes) | 2.9 | 3.1 | 3.0 | 3.25 |
| Crush Strength-lbs. | | | | |
| 15 minutes | 82 | 78 | 71 | 64 |
| 1 hour | 92 | 92 | 84 | 74 |
| 24 hours | 107 | 110 | 105 | 108 |

The above Examples illustrate the faster set times of the casting tapes of the present invention compared to set times of previous casting tapes. Although the set time of the cast are faster, the storage stability and strength of the casts are comparable to the casting tapes of the prior art.

EXAMPLE III

Two prepolymers were prepared with the isocyanate use in Example I. Prepolymer (a) was made with a hydrophilic polyol. Prepolymer (b) was made with mixtures of a hydrophobic diol (200 grams) and a hydrophobic triol (150 grams). The other ingredients in the formulations were substantially the same. Each prepolymer contained 2% by weight of dimorpholinodiethylether. The prepolymers were used in preparing casting tapes and test cylinders made as in Example I. The formulation made with the hydrophilic polyol had a faster set time than the formulation made with the hydrophobic polyols. The ultimate strength of the test cylinders made from the prepolymers were substantially similar. The formualtions and the results are shown in Table III. The ingredients in the table are shown in grams unless otherwise noted.

TABLE III

| | a | b |
|---|---|---|
| Isonate 143L | 547 | 600 |
| Polyol | 409 | 350 |
| Catalyst | 19 | 17 |
| Benzoyl Chloride | 0.4 cc | 0.4 cc |
| Silicone oil | .7 | .6 |
| Set Time (Minutes) | 2.8 | 4.3 |
| Crush Strength lbs. | | |
| 15 minutes | 59 | 61 |
| 1 hour | 76 | 83 |
| 24 hours | 94 | 92 |

I claim:

1. A storage stable fast setting orthopedic casting tape comprising a water activatable polyurethane prepolymer coated on a fibrous substrate, said prepolymer comprising an aromatic polyisocyanate and a polyol in an equivalent ratio of 2:1 to 15:1, said polyol being a hydrophilic polyol and having a molecular weight of from 200 to 6,000 and from one to 10 percent by weight, based on the total weight of the prepolymer formulation, of a dimorpholinodialkylether catalyst.

2. The casting tape of claim 1 in which the polyol is a poly(oxyalkyl) alcohol of the formula:

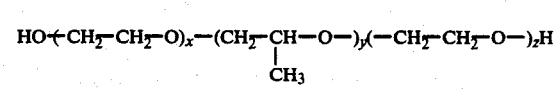

where x is at least 1 and y is between 3 and 42, and z may be 0 or an integer such that x+z is between 1 and 13.

3. The casting tape of claim 1 in which the polyol is a homopolymer of ethylene oxide.

4. The casting tape of claim 1 in which the polyol is a copolymer of ethylene oxide and propylene oxide containing no more than 80% by weight of propylene oxide.

5. The casting tape of claim 1 in which the polyol is a mixture of a hydrophilic polyol and a hydrophobic polyol, in which the hydrophobic polyol is no more than 80% by weight of the polyols.

6. The casting tape of claim 5 in which the mixture contains no more than 65% by weight of the hydrophobic polyol.

7. The casting tape of claim 4 containing no more than 65% by weight of propylene oxide.

8. The casting tape of claim 1 in which the polyol is a copolymer of ethylene oxide and tetramethylene oxide containing no more than 70% by weight of tetramethylene oxide.

9. The casting tape of claim 1 in which the equivalent ratio of isocyanate to polyol is from 2:1 to 10:1 and the molecular weight of the polyol is between 600 and 2000.

10. The casting tape of claim 1 in which the catalyst is dimorpholinodiethylether.

* * * * *